United States Patent
Baidossi et al.

(10) Patent No.: US 9,334,219 B2
(45) Date of Patent: May 10, 2016

(54) PROCESS FOR THE PREPARATION OF A STABLE POLYMORPHIC FORM OF ATOVAQUONE

(71) Applicant: TARO PHARMACEUTICAL INDUSTRIES LIMITED, Haifa Bay, Haifa (IL)

(72) Inventors: Wael Baidossi, Hamisholash (IL); Terese Soudah, Haifa (IL); Rosa Cyjon, Haifa-Bay (IL)

(73) Assignee: TARO PHARMACEUTICAL INDUSTRIES LTD., Haifa Bay (IL)

( * ) Notice: Subject to any disclaimer, the term of this patent is extended or adjusted under 35 U.S.C. 154(b) by 0 days.

(21) Appl. No.: 14/574,242

(22) Filed: Dec. 17, 2014

(65) Prior Publication Data
US 2015/0307431 A1   Oct. 29, 2015

Related U.S. Application Data

(63) Continuation of application No. 14/005,123, filed as application No. PCT/IL2012/050089 on Mar. 14, 2012, now abandoned.

(60) Provisional application No. 61/452,253, filed on Mar. 14, 2011.

(51) Int. Cl.
*C07C 45/81* (2006.01)
*C07C 46/00* (2006.01)

(52) U.S. Cl.
CPC ................ *C07C 46/00* (2013.01); *C07C 45/81* (2013.01); *C07B 2200/13* (2013.01)

(58) Field of Classification Search
CPC .......... C07C 45/81; C07C 50/32; C07C 46/00
USPC .................................................. 568/309, 324
See application file for complete search history.

(56) References Cited

U.S. PATENT DOCUMENTS

| 4,981,874 A | 1/1991 | Latter et al. ................... 514/682 |
| 5,053,432 A | 10/1991 | Hudson et al. ................. 514/682 |
| 2009/0105350 A1* | 4/2009 | Crasto et al. .................. 514/682 |
| 2010/0152302 A1* | 6/2010 | Parthasaradhi Reddy et al. ............................. 514/682 |

* cited by examiner

*Primary Examiner* — Sikarl Witherspoon

(57) ABSTRACT

The present invention provides a process for the preparation of a stable polymorph III of Atovaquone exhibiting characteristic peaks (expressed in degrees 2θ±0.2°θ) at about 6.9, 9.6, 14.1, 14.7, 17.0, 18.5, 19.1, 19.9, 20.3, 22.0, 22.6, 23.2, 24.2, 26.8, and 28.5, which comprises: (a) providing a sample of Atovaquone particles; (b) heating the sample of Atovaquone particles at a minimal temperature of between 140° C. to 160° C. depending on the particle size of the sample; and (c) cooling the sample to obtain the stable polymorphic form of Atovaquone.

30 Claims, 9 Drawing Sheets

| | PEAK NAME | PEAK LABEL | RT | RT RATIO | AREA | % AREA | USP RESOLUTION |
|---|---|---|---|---|---|---|---|
| 1 | DILUENT I | OTHER | 1.54 | 0.14 | 6375 74 | 0.01 | |
| 2 | DILUENT II | OTHER | 2.29 | 0.20 | 10743 13 | 0.02 | 2.72 |
| 3 | RRT=0.34 | RC | 3.70 | 0.33 | 1733.78 | 0.00 | 3.15 |
| 4 | RRT=0.39 | RC | 4.39 | 0.39 | 3698.09 | 0.01 | 1.69 |
| 5 | RRT=0.58 | RC | 6.61 | 0.58 | 7094.19 | 0.01 | 5.97 |
| 6 | RRT=0.81 | RC | 9.13 | 0.81 | 2438.95 | 0.00 | 5.96 |
| 7 | RELATED COMPOUND A | RC | 10.22 | 0.90 | 2863 85 | 0.00 | 2.48 |
| 8 | Atova QUONE | MAIN PEAK | 11.32 | | 68254563 97 | 99.91 | 2.36 |
| 9 | RRT=1.12 | RC | 12.65 | 1.12 | 8953.74 | 0.01 | |
| 10 | RRT=1.38 | RC | 15.61 | 1.38 | 2448 70 | 0.00 | |
| 11 | RRT=1.58 | RC | 17.81 | 1.57 | 3242.90 | 0.00 | 3.28 |
| 12 | RRT=1.95 | RC | 21.97 | 1.94 | 1500.63 | 0.00 | 5 94 |
| 13 | TRANS-INTERMEDIATE | RC | 24.15 | 2.13 | 8251 46 | 0.01 | 2 99 |

NON-MICRONIZED SAMPLE PRIOR TO THE HEATING STEP

FIG. 6A-1

|   | PEAK NAME | PEAK LABEL | RT | RT RATIO | AREA | % AREA | USP RESOLUTION |
|---|---|---|---|---|---|---|---|
| 1 | DILUENT I | OTHER | 1.33 | 0.14 | 9272.50 | 0.01 | |
| 2 | DILUENT II | OTHER | 1.59 | 0.16 | 7066.81 | 0.01 | 1.39 |
| 3 | DILUENT III | OTHER | 2.17 | 0.22 | 11260.61 | 0.02 | 2.16 |
| 4 | 4-CPCCA | RC | 2.80 | 0.28 | 1112.46 | 0.00 | 1.73 |
| 5 | RRT=0.41 | RC | 3.97 | 0.40 | 6002.21 | 0.01 | 3.52 |
| 6 | RRT=0.60 | RC | 5.82 | 0.59 | 13079.07 | 0.02 | 4.94 |
| 7 | RRT=0.81 | RC | 7.95 | 0.81 | 2611.16 | 0.00 | 4.76 |
| 8 | RELATED COMPOUND A | RC | 8.87 | 0.90 | 1610.42 | 0.00 | 2.08 |
| 9 | Atova QUONE | MAIN PEAK | 9.82 | | 63386645.98 | 99.91 | 2.02 |
| 10 | TRANS-INTERMEDIATE | RC | 20.83 | 2.12 | 7787.49 | 0.01 | 13.32 |

NON-MICRONIZED SAMPLE FOLLOWING THE HEATING STEP

FIG. 6B-1

PROCESS FOR THE PREPARATION OF A STABLE POLYMORPHIC FORM OF ATOVAQUONE

FIELD OF THE INVENTION

The present invention provides a feasible, simple and cost effective process for the preparation of a stable polymorphic form of (244-(4-Chlorophenyl)cyclohexyl]-3-hydroxy-1,4-naphthoquinone), commonly known as Atovaquone.

BACKGROUND OF THE INVENTION

Atovaquone is chemically described as trans 2-[4-(4-chlorophenyl)cyclohexyl]-3-hydroxy-1,4-naphthoquinone and has the following structure of formula 1:

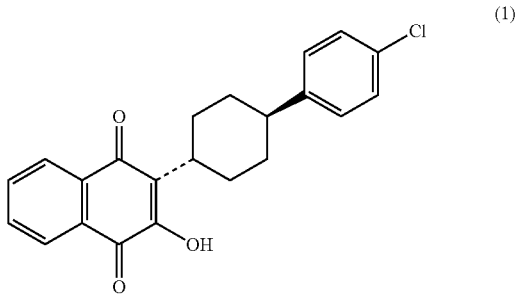

Atovaquone is an antiprotozoal agent and is useful in the treatment of *Pneumocystis carinii*, *Pneumocystis pneumonia*, Plasmodia, tachyzoite and cyst forms of *Toxoplasma gondii* and Malaria in combination with proguanil. Atovaquone is the active ingredient in two drugs, the first is an oral suspension (750 mg/5 mL) under the trade name Mepron® and is indicated for the treatment and prophylaxis of *Pneumocystis carinii* infection and the second drug is a combination with proguanil hydrochloride, under the brand name Malarone® tablets for the prophylaxis of Malaria. U.S. Pat. Nos. 4,981,874 and 5,053,432 describe Atovaquone and a pharmaceutical composition thereof and exemplify the crystallization of Atovaquone in acetonitrile.

Polymorphism is defined as "the ability of a substance to exist as two or more crystalline phases that have different arrangement and/or conformations of the molecules in the crystal lattice. Thus, polymorphs are different crystalline forms of the same pure substance in which the molecules have different arrangements and/or different configurations of the molecules. Different polymorphs may differ in their physical properties such as melting point, solubility, X-ray diffraction patterns, etc. Although these differences disappear once the compound is dissolved, they can appreciably influence pharmaceutically relevant properties of the solid form, such as handling properties, dissolution rate and stability. Such properties can significantly influence the processing, shelf life, and commercial acceptance of a polymorph. Polymorphic forms of a compound can be distinguished in the laboratory by analytical methods such as X-ray powder diffraction (XRPD), Differential Scanning calorimetry (DSC) and Infrared spectrometry (IR).

U.S. Publication No. 2009/0105350 describes a process for the preparation of Atovaquone polymorph III characterized by an X-ray powder diffraction pattern having peaks (expressed in degrees 2θ±0.2° 0) at about 7.0, 9.7, 14.2, 14.8, 17.0, 19.2, 20.4, 22.1, 22.7, 26.9 and 28.7. According to this publication, Atovaquone is dissolved in an aprotic polar solvent followed by the addition of a suitable antisolvent in order to precipitate and isolate Atovaquone polymorph III.

U.S. Publication No. 2010/0152302 discloses a crystallization process of Atovaquone using acetonitrile as a solvent, in order to obtain two polymorphic forms of Atovaquone, one of which, designated as "Form A", exhibited characteristic peaks (expressed in degrees 2θ±0.2° 0) at about 7.3, 10.0, 14.4, 15.1, 17.0, 18.8, 20.4, 22.2, 23.6, and 24.6. Form A was further characterized by Differential Scanning calorimetry (DSC) thermogram showing characteristic sharp endotherm at 221° C. The process for the preparation of Atovaquone "Form A" described in this publication, comprises treating Atovaquone with acetonitrile followed by cooling to a temperature of between about 0° C.-30° C. and isolating the obtained product.

The preparation of stable polymorphic forms of Atovaquone has the drawback of being expensive, time consuming, complicated and inappropriate to large scale manufacturing.

There remains a need to provide an alternative process for making Atovaquone which is cost-effective, feasible and highly reproducible on industrial scale to yield a stable polymorphic form on a consistent basis.

SUMMARY OF THE INVENTION

The present invention relates to a simple, feasible, cost-effective and commercially valuable process for the preparation of a stable polymorph III of Atovaquone which matches with the US Pharmacopea (USP) reference standard of Atovaquone. The process of the present invention provides high yield and purity of the stable polymorphic form of Atovaquone, useful for the preparation of pharmaceutical compositions.

In one embodiment, the present invention provides a process for the preparation of a stable polymorph III of Atovaquone which comprises:

(a) providing a sample of Atovaquone particles;
(b) heating the sample of Atovaquone particles of step (a) at a temperature of at least about 160° C. for a time sufficient to obtain a stable polymorphic form of Atovaquone, having characteristic peaks to (expressed in degrees 2θ±0.2° 0) at approximately one or more of the positions: about 6.9, 9.6, 14.1, 14.7, 17.0, 18.5, 19.1, 19.9, 20.3, 22.0, 22.6, 23.2, 24.2, 26.8, and 28.5; and
(c) cooling the sample of step (b).

In another embodiment, the present invention provides a process for the preparation of a stable polymorph III of Atovaquone which comprises:

(a) providing a sample of Atovaquone particles wherein at least about 90% of the Atovaquone particles have a volume diameter of equal or less than about 10µ;
(b) heating the sample of Atovaquone particles of step (a) at a temperature of at least about 140° C. for a time sufficient to obtain a stable polymorphic form of Atovaquone, having characteristic peaks (expressed in degrees 2θ±0.2° 0) at approximately one or more of the positions: about 6.9, 9.6, 14.1, 14.7, 17.0, 18.5, 19.1, 19.9, 20.3, 22.0, 22.6, 23.2, 24.2, 26.8, and 28.5; and (c) cooling the sample of step (b).

In another embodiment, the present invention provides a process for the preparation of a stable polymorph III of Atovaquone which comprises:

(a) providing a sample of Atovaquone particles wherein at least about 90% of the Atovaquone particles have a volume diameter of equal or less than about 40µ;
(b) heating the sample of Atovaquone particles of step (a) at a temperature of at least about 140° C. for a time sufficient to obtain a stable polymorphic form of Atovaquone, having characteristic peaks (expressed in degrees 2θ±0.2° O) at approximately one or more of the positions: about 6.9, 9.6, 14.1, 14.7, 17.0, 18.5, 19.1, 19.9, 20.3, 22.0, 22.6, 23.2, 24.2, 26.8, and 28.5; and (c) cooling the sample of step (b).

In another embodiment, the present invention provides a stable polymorph III of Atovaquone, having a chemical purity of at least about 99.5 percent.

In another embodiment, the process of the present invention provides a stable polymorphic form of Atovaquone which can be used for the preparation of pharmaceutical compositions.

BRIEF DESCRIPTION OF THE DRAWINGS

The subject matter regarded as the invention is particularly pointed out and distinctly claimed in the concluding portion of the specification. The invention, however, both s to organization and method of operation, together with objects, features, and advantages thereof, may best be understood by reference to the following detailed description when read with the accompanying drawings in which:

(FIG. 6A); Table of Peaks: FIG. 6A-1) and following the heating step (Chromatogram: FIG. 6B-1).

Figure 1A:
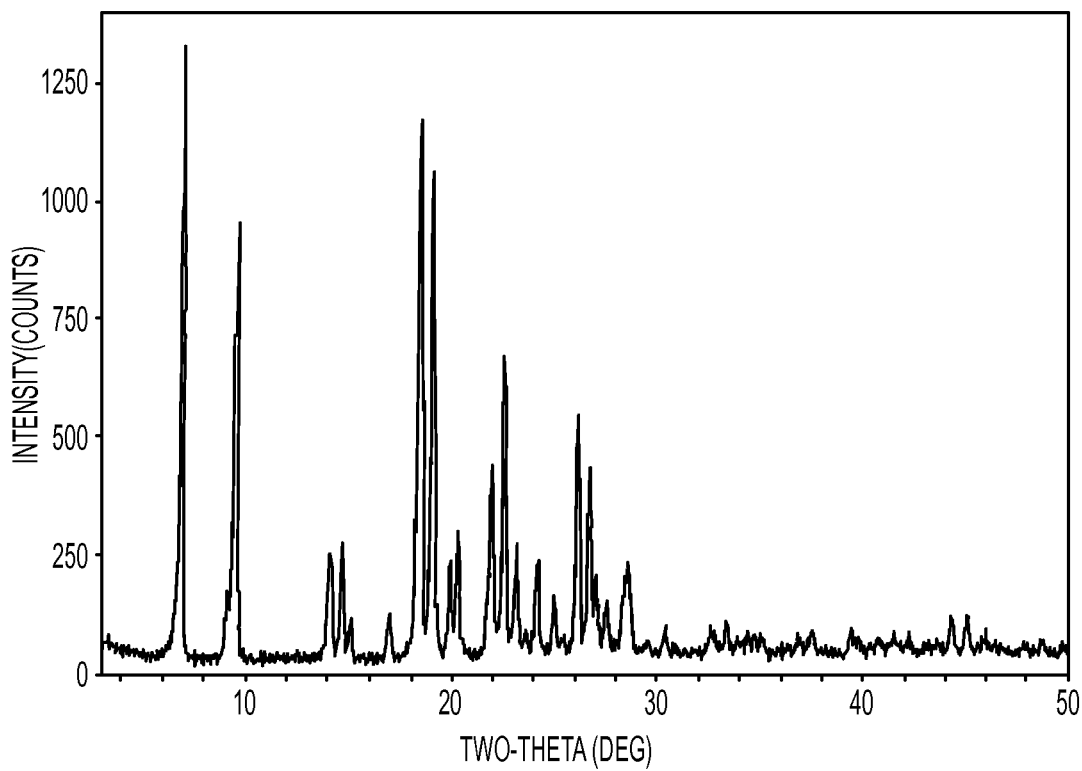
FIGS. 1A-B depict characteristic X-ray powder diffraction (XRPD) pattern (FIG. 1A) and Differential Scanning calorimetry (DSC) thermogram (FIG. 1B) of the USP reference standard of Atovaquone.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE PRESENT INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

The term "polymorphic form of Atovaquone" as used herein, refers to polymorph III of Atovaquone which matches with the USP reference standard of Atovaquone, having characteristic peaks (expressed in degrees 2θ±0.2° 0) at approximately one or more of the positions: about 6.9, 9.6, 14.1, 14.7, 17.0, 18.5, 19.1, 19.9, 20.3, 22.0, 22.6, 23.2, 24.2, 26.8, and 28.5.

The term "stable polymorphic form" as used herein refers to a polymorphic form which is stable thermodynamically and is formed by an irreversible conversion of the polymorphic form of the sample to polymorph III of Atovaquone, the polymorphic form which matches with the USP reference standard.

The term "Atovaquone particles" as used herein, refers to Atovaquone particles of any crystalline or amorphous form or a mixture thereof which are used in the process of the present invention as a starting material.

The term "micronized" as used herein, refers to Atovaquone particles wherein at least about 90% of the particles having a volume diameter of equal or less than about 10μ.

The term "non-micronized" as used herein, refers to Atovaquone particles wherein at least about 90% of the particles having a volume diameter of greater than about 10μ.

The term "about" as used herein, refers to a deviance of between 0.0001-10% from the indicated number or range of numbers.

The term "purity" refers to the chemical purity of the stable polymorph III of Atovaquone as determined by a conventional HPLC assay.

The term "total impurities" refers to the sum of all chemical impurities produced during the preparation process for the stable polymorph III of Atovaquone as determined by a conventional HPLC assay.

The term "approximately" and "about" refer to a deviance of between 0.0001-5% from the indicated number or range of numbers. In one embodiment, the term "approximately" and "about", refer to a deviance of between 1-10% from the indicated number or range of numbers.

In one embodiment, the present invention provides a process for the preparation of a stable polymorph III of Atovaquone which comprises:

(a) providing a sample of Atovaquone particles;

(b) heating the sample of Atovaquone particles of step (a) at a temperature of at least about 160° C. for a time sufficient to obtain a stable polymorphic form of Atovaquone, having characteristic peaks (expressed in degrees 2θ±0.2° 0) at approximately one or more of the positions: about 6.9, 9.6, 14.1, 14.7, 17.0, 18.5, 19.1, 19.9, 20.3, 22.0, 22.6, 23.2, 24.2, 26.8, and 28.5; and (c) cooling the sample of step (b).

The sample of Atovaquone particles used in the first step may comprise either micronized or non-micronized particles. In one embodiment, micronized particles of Atovaquone are used as a starting material in step (a) in which at least about 90% of the micronized particles have a volume diameter of equal or less than about 10μ. Preferably, at least 90% of the particles have a volume diameter in the range of between about 4μ to about 10μ. More preferably, the particles have a volume diameter in the range of between about 8μ to about 10μ or between 4μ to 6μ.

If non-micronized Atovaquone particles are used in step (a), or if further micronization is required, the sample of step (c) may be micronized to obtain Atovaquone particles having particle volume diameter in which at least about 90% of the Atovaquone particles have a volume diameter of equal or less than about 10μ. Preferably, the Atovaquone particles following micronization have a volume diameter in which at least about 90% of the particles are in the range of between 4μ to 10μ. More preferably, the Atovaquone particles following micronization have a volume diameter in which at least about 90% of the particles are in the range of between 8μ, to 10μ, or between 4μ to 6μ.

In another embodiment, the process of the invention comprises:
- (a) providing a sample of Atovaquone particles wherein at least about 90% of the Atovaquone particles have a volume diameter of equal or less than about 40μ;
- (b) heating the sample of Atovaquone particles of step (a) at a temperature of at least about 140° C. for a time sufficient to obtain a stable polymorphic form of Atovaquone, having characteristic peaks (expressed in degrees 2θ±0.2° 0) at approximately one or more of the positions: about 6.9, 9.6, 14.1, 14.7, 17.0, 18.5, 19.1, 19.9, 20.3, 22.0, 22.6, 23.2, 24.2, 26.8, and 28.5; and
- (c) cooling the sample of step (b).

In another embodiment, the present invention provides a process for the preparation of a stable polymorph III of Atovaquone which comprises:
- (a) providing a sample of Atovaquone particles wherein at least about 90% of the Atovaquone particles have a volume diameter of equal or less than about 10μ;
- (b) heating the sample of Atovaquone particles of step (a) at a temperature of at least about 140° C. for a time sufficient to obtain a stable polymorphic form of Atovaquone, having characteristic peaks (expressed in degrees 2θ±0.2° 0) at approximately one or more of the positions: about 6.9, 9.6, 14.1, 14.7, 17.0, 18.5, 19.1, 19.9, 20.3, 22.0, 22.6, 23.2, 24.2, 26.8, and 28.5; and
- (c) cooling the sample of step (b).

The sample of Atovaquone particles used in the process of the present invention as a starting material may comprise any polymorphic or amorphous forms of Atovaquone which is obtained by any process for preparing Atovaquone known in the art. Such process is disclosed for example in U.S. Pat. No. 4,981,874, the content of which is incorporated herein by reference.

In one embodiment, the Atovaquone sample provided in step (a) comprises Atovaquone particles wherein at least about 90% of the Atovaquone particles have a volume diameter of equal or less than about 100μ.

In another embodiment, the Atovaquone sample provided in step (a) comprises Atovaquone particles wherein at least about 90% of the Atovaquone particles have a volume diameter of equal or less than about 50μ.

In another embodiment, the Atovaquone sample provided in step (a) comprises Atovaquone particles wherein at least about 90% of the Atovaquone particles have a volume diameter of equal or less than about 25μ.

In another embodiment, the Atovaquone sample provided in step (a) comprises Atovaquone particles wherein at least about 90% of the Atovaquone particles have a volume diameter of equal or less than about 10μ.

It is appreciated that when larger particle size of Atovaquone are used in step (a), it will require longer heating time or higher temperatures during the heating step, or a combination thereof in order to obtain the desired polymorphic form of Atovaquone.

In one embodiment, the Atovaquone sample is exposed to a minimal temperature of about 160° C. during the heating step. In another embodiment, the Atovaquone sample is exposed to a minimal temperature of about 140° C. during the heating step. In another embodiment, the Atovaquone sample is exposed to a minimal temperature of about 120° C. during the heating step. In another embodiment, the Atovaquone sample is exposed to a minimal temperature of about 100° C. during the heating step.

In one embodiment, the Atovaquone sample is exposed to heating time of about 24 hours during the heating step. In another embodiment, the Atovaquone sample is exposed to heating time of about 12 hours during the heating step. In another embodiment, the Atovaquone sample is exposed to heating time of about 6 hours during the heating step. In another embodiment, the Atovaquone sample is exposed to heating time of about 4 hours during the heating step. In another embodiment, the Atovaquone sample is exposed to heating time of about 2 hours during the heating step. In another embodiment, the Atovaquone sample is exposed to heating time of about 1 hour during the heating step. In another embodiment, the Atovaquone sample is exposed to heating time of at least about 1 hour.

The heating step is carried out for a sufficient time to allow the conversion of all polymorphs in the sample to a stable polymorph III of Atovaquone which matches with the USP reference standard of Atovaquone. More specifically, the heating can be carried out for about 1 to about 24 hours, more preferably for about 1 to about 3 hours, most preferably for about 2 hours.

In one embodiment, the process of this invention includes a heating step for a time sufficient to obtain a stable polymorphic form III of Atovaquone, having characteristic peaks (expressed in degrees 2θ±0.2° 0) at approximately one or more of the positions: about 6.9, 9.6, 14.1, 14.7, 17.0, 18.5, 19.1, 19.9, 20.3, 22.0, 22.6, 23.2, 24.2, 26.8, and 28.5. In another embodiment, the stable polymorphic form III of Atovaquone of this invention has characteristic peaks (expressed in degrees 2θ±0.2° 0) at approximately about 6.9, 9.6, 14.1, 14.7, 17.0, 18.5, 19.1, 19.9, 20.3, 22.0, 22.6, 23.2, 24.2, 26.8, and 28.5. In another embodiment, the stable polymorphic form III of Atovaquone of this invention has characteristic peaks (expressed in degrees 2θ±0.2° 0) at approximately about 6.9, 9.6, 14.1, 14.7, 19.9, 20.3, 22.0, 22.6, 24.2 and 26.8. In another embodiment, the stable polymorphic form of Atovaquone of this invention has peaks in X-ray powder diffraction characteristic to Form III of Atovaquone.

In the third step, the Atovaquone sample is cooled to a temperature from about 20° C. to about 40° C. for about 1 hour to about 24 hours. The Atovaquone sample of the present invention is subjected to a Powder X-ray Diffractometer and differential scanning calorimetry (DSC) in order to verify that polymorph III of Atovaquone which matches with the USP reference standard was obtained.

The stable polymorphic form of Atovaquone obtained by the process of the present invention has a chemical purity as measured by HPLC of at least about 98%, preferably a chemical purity of at least about 99%, more preferably a chemical purity of at least about 99.5% and most preferably a chemical purity of about 99.9% or higher. Furthermore, the stable polymorphic form of Atovaquone obtained by the process of the present invention has total impurities as measured by HPLC of not more than about 0.5 area percent (%).

EXAMPLES

The following examples are presented in order to more fully illustrate the preferred embodiments of the invention. However, they should in no way be construed as limiting the broad scope of the invention.

Methods

The polymorphic form of Atovaquone was characterized by X-ray powder diffraction pattern using a Powder X-ray Diffractometer (RIGAKU) with a copper-Kα-40 KV radiation of k=1.54059 Å. The measurements were carried out from 3 to 50 degrees.

The polymorphic form of Atovaquone was further characterized by Differential Scanning calorimetry (DSC). Measurements of thermal analysis were conducted for the purpose of evaluating the physical and chemical changes that may take place in a heated sample. Thermal reactions can be endothermic (e.g., melting, boiling, sublimation, vaporization, desolvation, solid-solid phase transitions, chemical degradation, etc.) or exothermic (e.g., crystallization, oxidative decomposition, etc.) in nature. The DSC curves presented herein were obtained by using the method which is as follows:

Approximately 1-5 mg of sample was accurately weighed into an aluminum DSC pan with lid. The sample was then placed into a Mettler Toledo DSC821$^e$ equipped with a liquid nitrogen cooling unit and allowed to equilibrate at 30° C. until stable heat flow response was seen. A dry nitrogen purge gas at a flow rate of 50 ml/min was used to produce the inert atmosphere and prevent oxidation of the sample during heating. The sample was scanned from 30 to 300° C. at rate of 10° C./min in a standard Alumina crucibles covered with lids with on hole and resulting heat flow response was measured against temperature.

Example 1

Figure 1B:
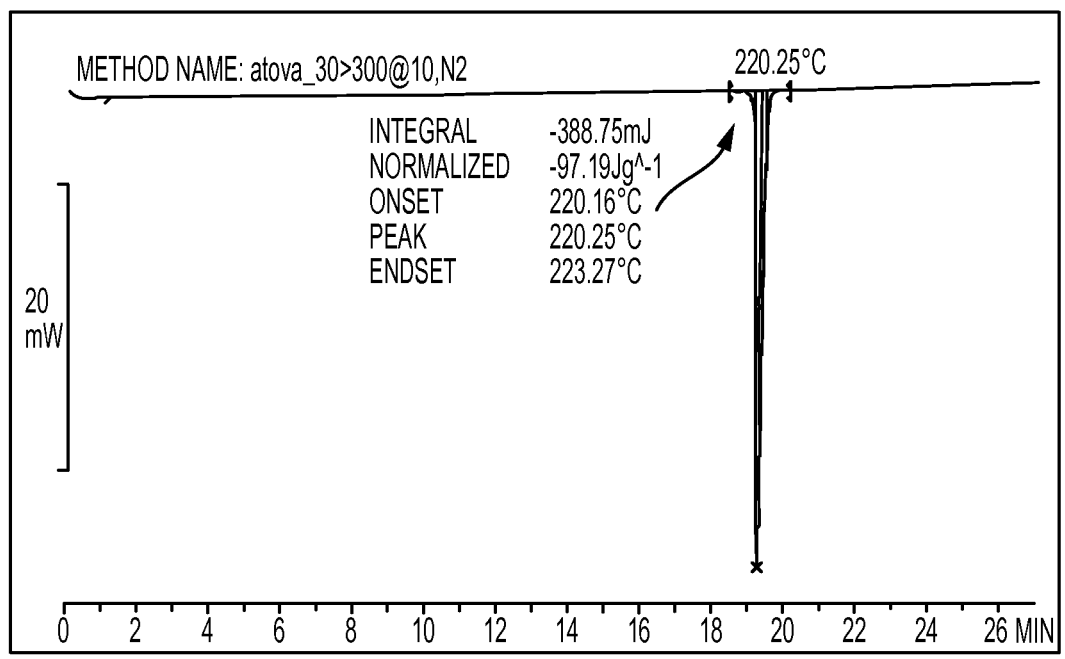
Figure 2A:
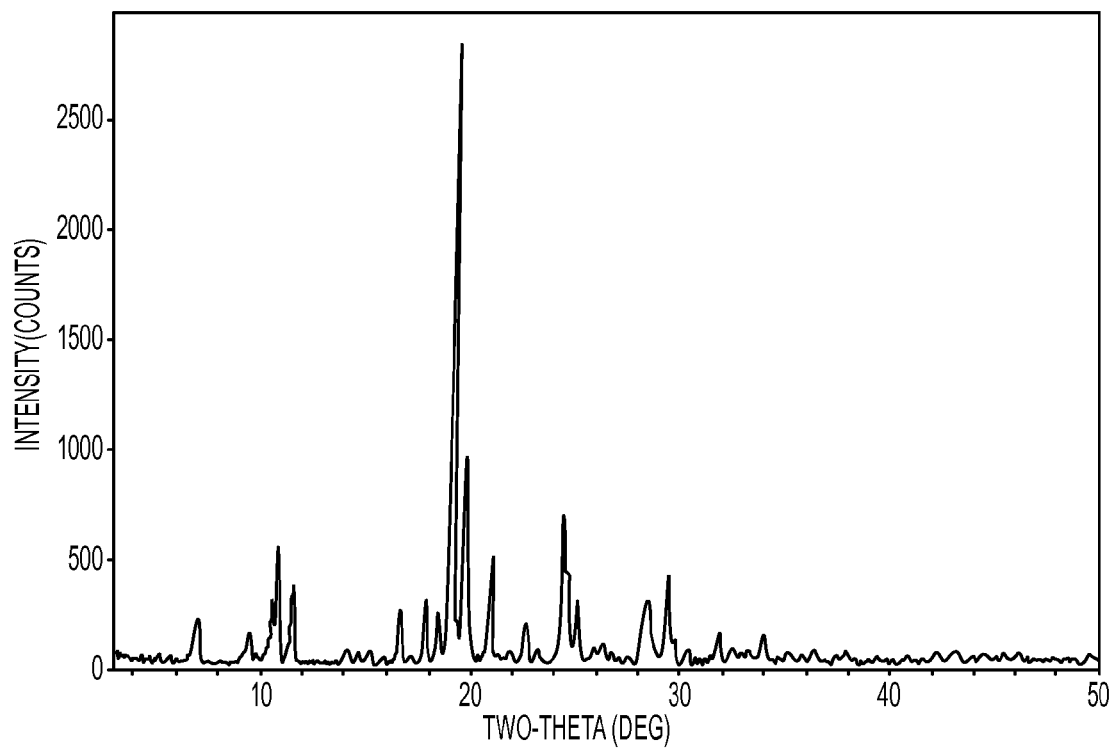
FIGS. 2A-B depict characteristic XRPD pattern (FIG. 2A) and DSC thermogram (FIG. 2B) of a sample of non-micronized Atovaquone particles prior to the heating step.
Figure 2B:
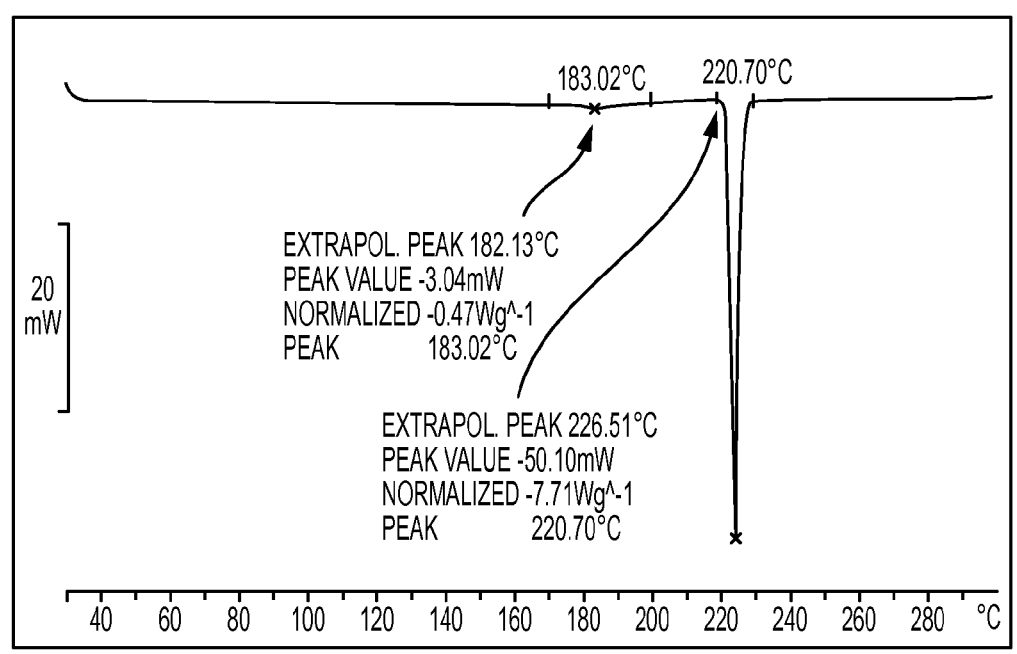

Atovaquone USP reference standard lot # GOH328 was subjected to X-ray powder diffraction analysis and differential scanning calorimetry (DSC) as described above and as shown in FIGS. 1A and 1B respectively. The X-ray powder diffraction analysis for the Atovaquone USP reference standard lot # GOH328 is also set forth in table 1 below.

terized by a DSC thermogram pattern with a small endotherm peak at 183° C. followed by a sharp endotherm peak at 220° C., as illustrated in FIG. 2B. The sample was inserted into a tray Turbo oven and heated for 2 hours at a temperature of about 170° C. followed by cooling to a temperature of between about 25° C. to about 30° C.

Figure 3A:
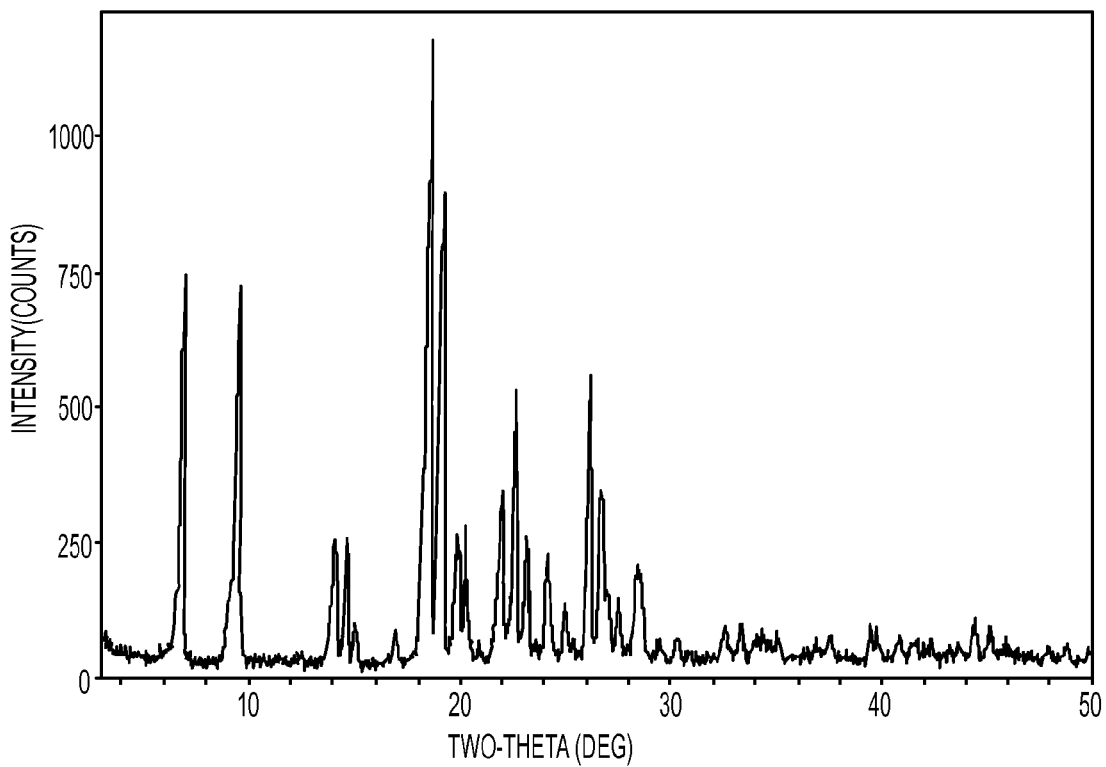
FIGS. 3A-B depict characteristic XRPD pattern (FIG. 3A) and DSC thermogram (FIG. 3B) of a sample of non-micronized Atovaquone particles following the heating step.
Figure 3B:
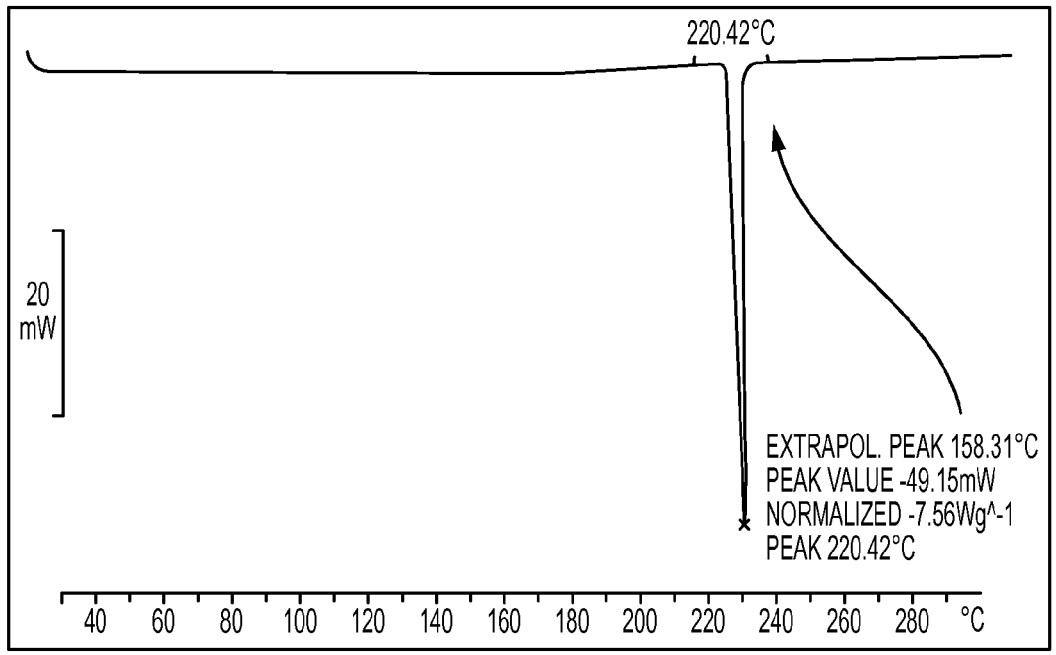

As demonstrated in FIG. 3B, the sample following 2 hours of heating contained a polymorph of Atovaquone characterized by DSC thermogram pattern comparable to the USP standard (polymorph III) with a single endotherm peak at 220° C. The disappearance of the peak at 183° C. in the DSC thermogram following the heating step demonstrates the conversion of all polymorphic forms of Atovaquone in the sample to polymorph III. The polymorph of Atovaquone was further characterized by X-ray powder diffraction and the pattern obtained also matched with the USP standard (see FIG. 3A and Table 1).

Example 3

Figure 4A:
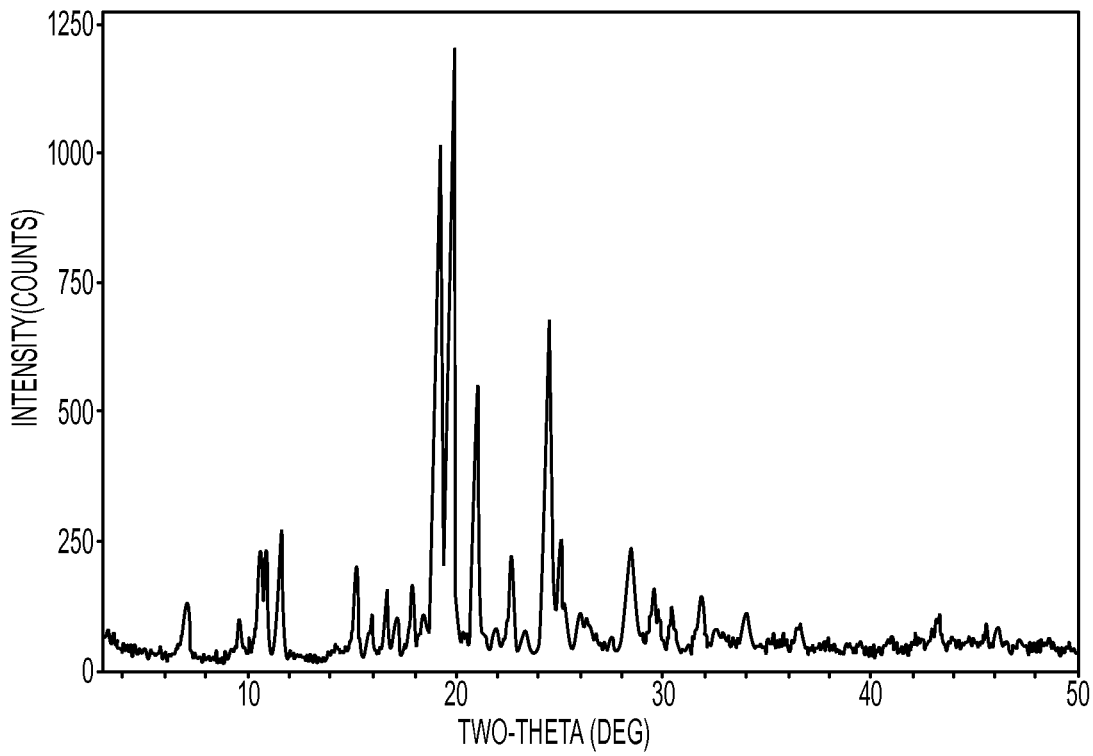
FIGS. 4A-B depict characteristic XRPD pattern (FIG. 4A) and DSC thermogram (FIG. 4B) of a sample of micronized Atovaquone particles prior to the heating step.
Figure 4B:
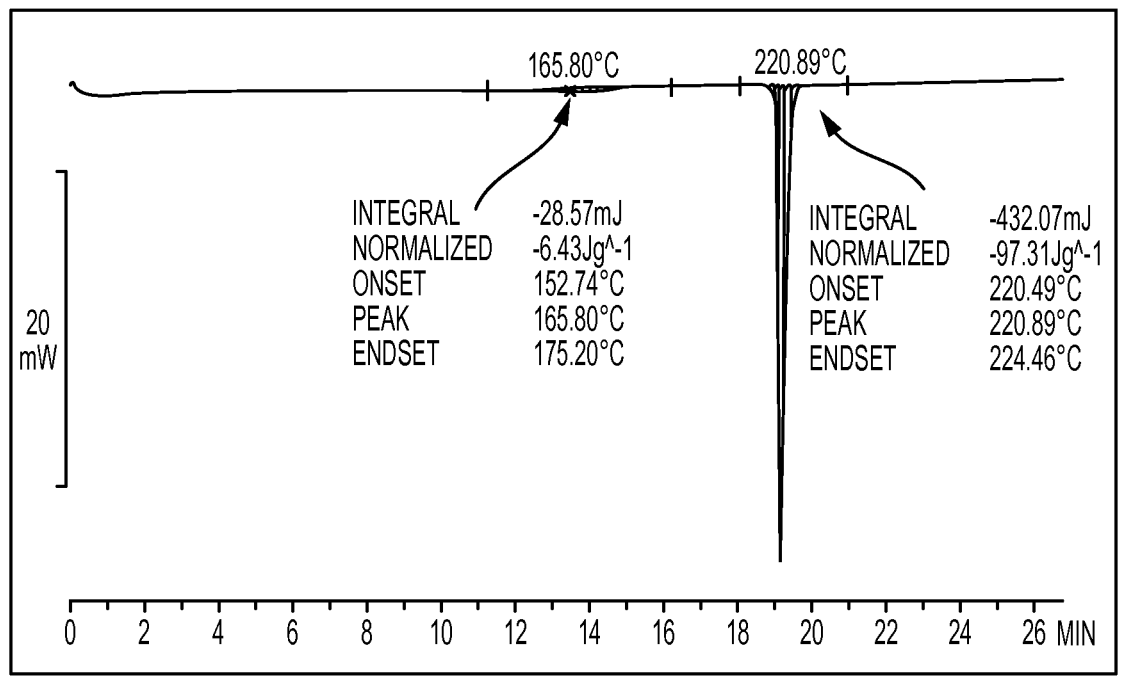

An Atovaquone sample (obtained by the process disclosed in U.S. Pat. No. 5,053,432) which comprises a mixture of polymorphic forms of Atovaquone or a single polymorphic form was characterized by DSC thermogram pattern with a small endotherm peak at 165° C. followed by a sharp endotherm peak at 220° C., as shown in FIG. 4B. The Atovaquone sample was then micronized in order to obtain micronized particles in which about 90% of particles having a volume diameter of 9.1μ, or less. The micronized particles of Atovaquone were then inserted into a tray Turbo oven and heated for 2 hours at a temperature of about 150° C. followed by cooling to a temperature of between about 25° C. to about 30° C.

TABLE 1

| USP Standard Lot # GOH328) Example 1 | | | Atovaquone sample (Non-micronized) Example 2 | | | Atovaquone sample (Micronized) Example 3 | | |
|---|---|---|---|---|---|---|---|---|
| Pos, [2° TH.] | d-spacing [Å] | Rel. Int. [%] | Pos. [2° TH.] | d-spacing [Å] | Rel. Int. [%] | Pos. [2° TH.] | d-spacing [Å] | Rel. Int. [%] |
| 6.939 | 12.7281 | 37.4 | 6.882 | 12.8346 | 49.3 | 6.919 | 12.7658 | 65.9 |
| 9.600 | 9.2052 | 43.5 | 9.540 | 9.2637 | 62.1 | 9.578 | 9.2267 | 62.2 |
| 14.102 | 6.2753 | 14.3 | 14.080 | 6.2848 | 22.9 | 14.140 | 6.2583 | 21.9 |
| 14.741 | 6.0047 | 13.4 | 14.661 | 6.0373 | 18.1 | 14.717 | 6.0143 | 16.2 |
| 16.999 | 5.2116 | 8.8 | 16.958 | 5.2241 | 3.6 | 16.979 | 5.2178 | 5.3 |
| 18.460 | 4.8024 | 100.0 | 18.439 | 4.8078 | 100.0 | 18.518 | 4.7875 | 100.0 |
| 19.140 | 4.6333 | 88.4 | 19.100 | 4.6430 | 68.1 | 19.101 | 4.6427 | 63.1 |
| 20.022 | 4.4312 | 25.0 | 19.919 | 4.4538 | 24.0 | 20.035 | 4.4282 | 27.1 |
| 20.397 | 4.3504 | 38.1 | 20.317 | 4.3675 | 17.6 | 20.343 | 4.3620 | 18.3 |
| 22.002 | 4.0367 | 49.9 | 21.980 | 4.0407 | 30.6 | 22.002 | 4.0366 | 34.2 |
| 22.641 | 3.9241 | 61.0 | 22.599 | 3.9313 | 37.5 | 22.640 | 3.9244 | 43.7 |
| 23.201 | 3.8307 | 22.4 | 23.180 | 3.8341 | 17.1 | 23.203 | 3.8302 | 14.3 |
| 24.297 | 3.6603 | 9.2 | 24.180 | 3.6777 | 13.6 | 24.240 | 3.6688 | 14.3 |
| 25.063 | 3.5502 | 7.3 | 25.004 | 3.5584 | 5.8 | 25.044 | 3.5528 | 7.5 |
| 26.241 | 3.3934 | 40.9 | 26.144 | 3.4057 | 30.2 | 26.220 | 3.3961 | 32.2 |
| 26.838 | 3.3192 | 52.3 | 26.758 | 3.3290 | 33.4 | 26.799 | 3.3240 | 32.6 |
| 27.175 | 3.2788 | 24.1 | 27.100 | 3.2877 | 15.2 | 27.098 | 3.2880 | 12.2 |
| 27.606 | 3.2286 | 3.2 | 27.543 | 3.2359 | 4.3 | 27.657 | 3.2228 | 3.8 |
| 28.700 | 3.1079 | 24.3 | 28.480 | 3.1315 | 19.9 | 28.641 | 3.1143 | 22.1 |

Example 2

A sample of non-micronized particles of Atovaquone, (obtained by the process disclosed in U.S. Pat. No. 5,053,432) was used in this Example. Analysis of the volume diameter of the particles used in this Example revealed that 90% of the particles have a volume diameter of 88μ or less.

Figure 5A:
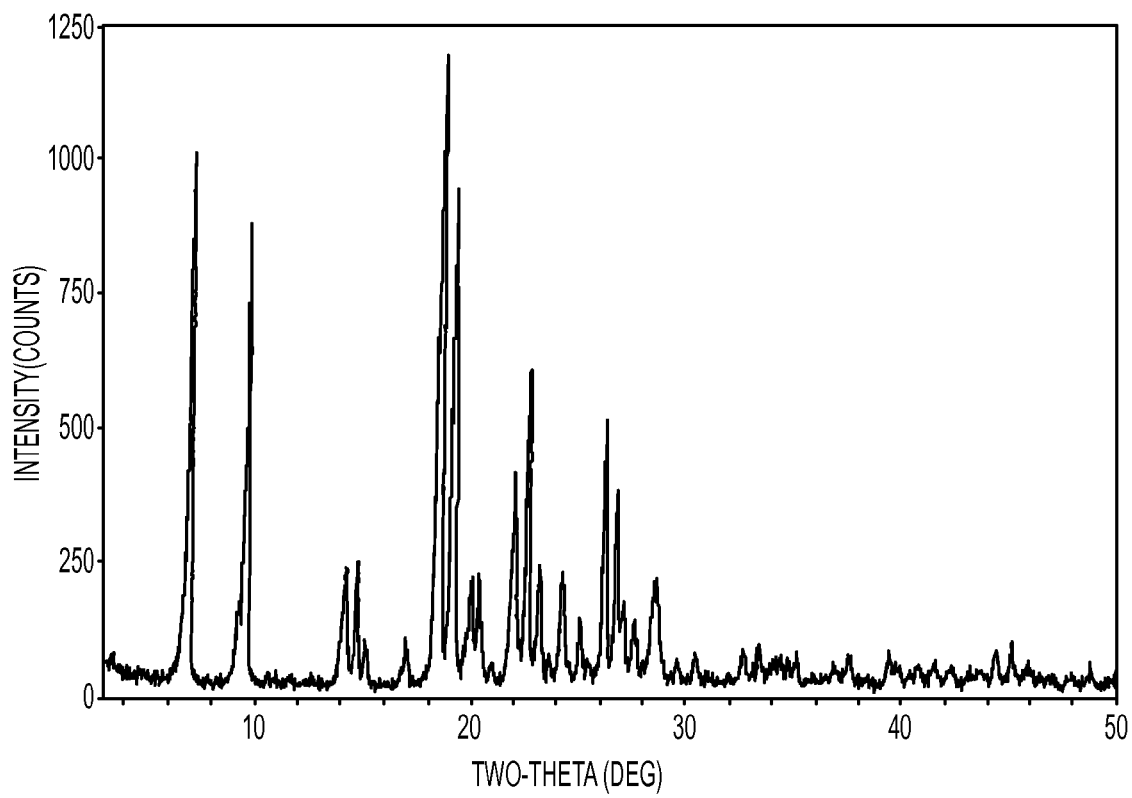
FIGS. 5A-B depict characteristic XRPD pattern (FIG. SA) and DSC thermogram (FIG. 5B) of a sample of micronized Atovaquone particles following the heating step.
Figure 5B:
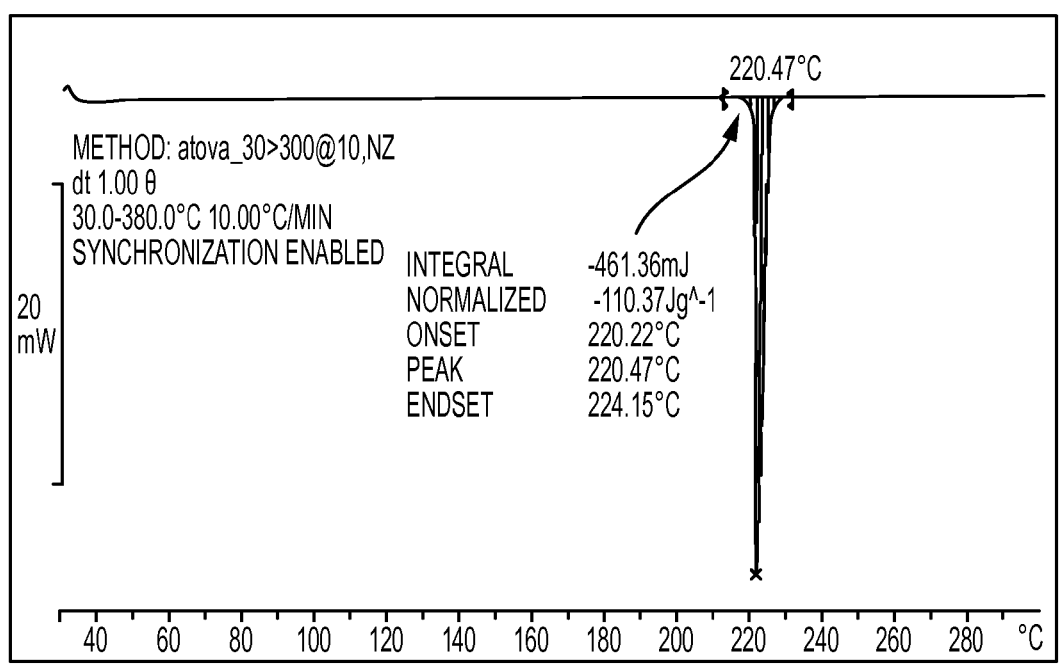

The sample comprises a mixture of different polymorphic forms of Atovaquone or a single polymorphic form charac- As demonstrated in FIG. 5B, the sample following 2 hours of heating contained a polymorph of Atovaquone characterized by DSC thermogram pattern comparable to polymorph III with a single endotherm peak at 220° C. The disappearance of the peak at 165° C. in the DSC thermogram following the heating step demonstrates the conversion of all polymorphic forms of Atovaquone in the sample to polymorph III. The polymorph of Atovaquone was further characterized by X-ray powder diffraction and the pattern obtained also matched with the USP standard (see FIG. 5A and Table 1).

Example 4

Figure 6A:
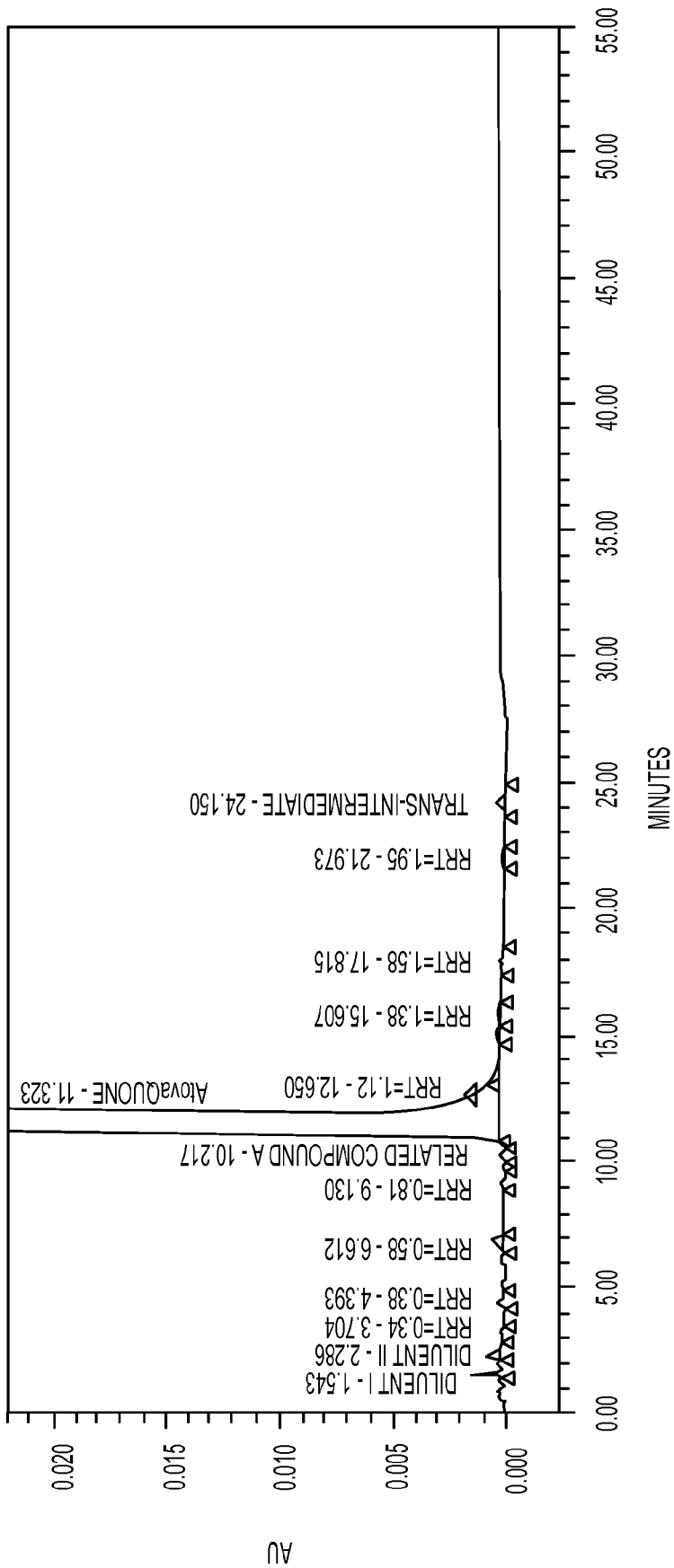
FIGS. 6A-B1 depict a high performance liquid chromatography (HPLC) analysis of a sample of non-micronized Atovaquone particles prior to heating (Chromatogram.
Figure 6B:
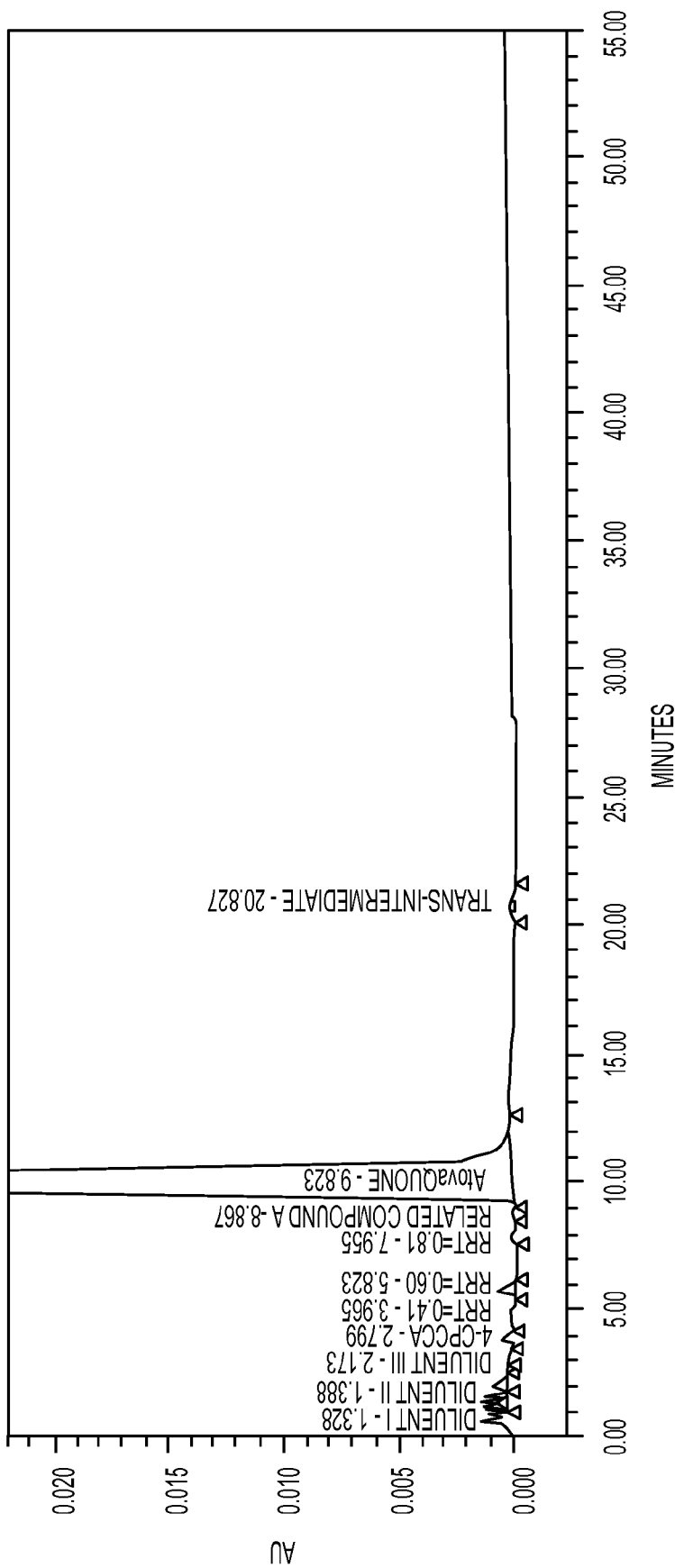
(FIG. 6B); Table of Peaks.

The chemical purity of the Atovaquone sample was analyzed by high performance liquid chromatography (HPLC) prior to and following the heating step which was described above, in order to demonstrate that the chemical purity of the sample was not affected by the high temperature treatment. An Atovaquone sample (50 mg) of non-micronized particles was dissolved in acetonitrile and was applied to a HPLC column (XBridge C18, 150×3.0 mm, 3.5 µm) at a temperature of 30° C. Chromatography was then carried out with a solvent system of 0.1% Phosphoric acid and Acetonitrile (32:68, v/v) using a flow rate gradient of 0.5 ml/min at 0-24 minutes, 0.8 ml/min at 25-54 minutes and 0.5 ml/min at 55 minutes. FIGS. 6A-6B show two HPLC charts obtained with the non-micronized particles of Atovaquone prior to the heating step (FIG. 6A) and following 2 hours of heating (FIG. 6B). In both cases, a chemical purity of 99.91% was obtained. An HPLC analysis of micronized particles of Atovaquone prior to and following 2 hours of heating revealed similar purity values.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

We claim:

1. A process for the preparation of a stable polymorph III of Atovaquone which comprises:
    a) providing a sample of Atovaquone particles;
    b) heating the sample of Atovaquone particles of step (a) at a temperature of at least about 160° C. for a time sufficient of at least about one hour to obtain a stable polymorphic form of Atovaquone, having characteristic peaks (expressed in degrees 2θ±0.2° θ) at approximately one or more of the positions: about 6.9, 9.6, 14.1, 14.7, 17.0, 18.5, 19.1, 19.9, 20.3, 22.0, 22.6, 23.2, 24.2, 26.8, and 28.5; and
    c) cooling the sample of step (b);
wherein the process is carried out in the absence of a solvent.

2. A process for the preparation of a stable polymorph III of Atovaquone which comprises:
    a) providing a sample of Atovaquone particles wherein at least about 90% of the Atovaquone particles have a volume diameter of equal or less than about 40µ;
    b) heating the sample of Atovaquone particles of step (a) at a temperature of at least about 140° C. for a time sufficient to obtain a stable polymorphic form of Atovaquone, having characteristic peaks (expressed in degrees 2θ±0.2° θ) at approximately one or more of the positions about 6.9, 9.6, 14.1, 14.7, 17.0, 18.5, 19.1, 19.9, 20.3, 22.0, 22.6, 23.2, 24.2, 26.8, and 28.5; and
    c) cooling the sample of step (b);
wherein the process is carried out in the absence of a solvent.

3. The process of claim 1, wherein the Atovaquone particles of step (c) are further micronized if non-micronized particles are used in step (a), to obtain Atovaquone particles having particle volume diameter suitable for the preparation of pharmaceutical compositions of Atovaquone.

4. The process of claim 3, wherein at least about 90% of the Atovaquone particles have a volume diameter of equal or less than about 10µ following micronization.

5. The process of claim 4, wherein at least about 90% of the Atovaquone particles have a volume diameter in the range of between 4µ to 10µ.

6. The process of claim 5, wherein at least about 90% of the Atovaquone particles have a volume diameter in the range of between 8µ to 10µ or between 4µ to 6µ.

7. The process of claim 1, wherein the heating time sufficient to obtain the stable polymorphic form of Atovaquone is between about 1 hour to about 24 hours.

8. The process of claim 1, wherein the sample is cooled to a temperature of between about 20° C. to about 40° C.

9. The process of claim 1, wherein the stable polymorph III of Atovaquone has a chemical purity of at least about 99.5 percent.

10. The process of claim 9, wherein the stable polymorph III of Atovaquone has a chemical purity of at least about 99.9 percent.

11. The process of claim 1, wherein the stable polymorph III of Atovaquone has total chemical impurities of not more than about 0.5 area percent.

12. A process for the preparation of a stable polymorph III of Atovaquone which comprises:
    a) providing a sample of Atovaquone particles wherein at least about 90% of the Atovaquone particles have a volume diameter of equal or less than about 10µ;
    b) heating the sample of Atovaquone particles of step (a) at a temperature of at least about 140° C. for a time sufficient to obtain a stable polymorphic form of Atovaquone, having characteristic peaks (expressed in degrees 2θ±0.2° θ) at approximately one or more of the positions about 6.9, 9.6, 14.1, 14.7, 17.0, 18.5, 19.1, 19.9, 20.3, 22.0, 22.6, 23.2, 24.2, 26.8, and 28.5; and
    c) cooling the sample of step (b);
wherein the process is carried out in the absence of a solvent.

13. The process of claim 12, wherein at least about 90% of the Atovaquone particles of step (a) have a volume diameter in the range of between 4µ to 10µ.

14. The process of claim 13, wherein at least about 90% of the Atovaquone particles of step (a) have a volume diameter in the range of between 8µ to 10µ or between 4µ to 6µ.

15. The process of claim 12, wherein the heating time sufficient to obtain the stable polymorphic form of Atovaquone is between about 1 hour to about 24 hours.

16. The process of claim 15, wherein the heating time sufficient to obtain the stable polymorphic form of Atovaquone is between about 1 hour to about 3 hours.

17. The process of claim 16, wherein the heating time sufficient to obtain the stable polymorphic form of Atovaquone is about 2 hours.

18. The process of claim 12, wherein the sample is cooled to a temperature of between about 20° C. to about 40° C.

19. The process of claim 12, wherein the stable polymorph III of Atovaquone has a chemical purity of at least about 99.5 percent.

20. The process of claim 19, wherein the stable polymorph III of Atovaquone has a chemical purity of at least about 99.9 percent.

21. The process of claim 12, wherein the stable polymorph III of Atovaquone has total chemical impurities of not more than about 0.5 area percent.

22. The process of claim 2, wherein the Atovaquone particles of step (c) are further micronized if non-micronized particles are used in step (a), to obtain Atovaquone particles having particle volume diameter suitable for the preparation of pharmaceutical compositions of Atovaquone.

23. The process of claim 22, wherein at least about 90% of the Atovaquone particles have a volume diameter of equal or less than about 10μ following micronization.

24. The process of claim 23, wherein at least about 90% of the Atovaquone particles have a volume diameter in the range of between 4μ to 10μ.

25. The process of claim 24, wherein at least about 90% of the Atovaquone particles have a volume diameter in the range of between 8μ to 10μ or between 4μ to 6μ.

26. The process of claim 2, wherein the heating time sufficient to obtain the stable polymorphic form of Atovaquone is between about 1 hour to about 24 hours.

27. The process of claim 2, wherein the sample is cooled to a temperature of between about 20° C. to about 40° C.

28. The process of claim 2, wherein the stable polymorph III of Atovaquone has a chemical purity of at least about 99.5 percent.

29. The process of claim 28, wherein the stable polymorph III of Atovaquone has a chemical purity of at least about 99.9 percent.

30. The process of claim 2, wherein the stable polymorph III of Atovaquone has total chemical impurities of not more than about 0.5 area percent.

* * * * *